US008343131B2

(12) United States Patent
Vinten-Johansen

(10) Patent No.: US 8,343,131 B2
(45) Date of Patent: Jan. 1, 2013

(54) CATHETER FOR MODIFIED PERFUSION

(75) Inventor: Jakob Vinten-Johansen, Grayson, GA (US)

(73) Assignee: Emory University, Atlanta, GA (US)

( * ) Notice: Subject to any disclaimer, the term of this patent is extended or adjusted under 35 U.S.C. 154(b) by 432 days.

(21) Appl. No.: 12/748,049

(22) Filed: Mar. 26, 2010

(65) Prior Publication Data

US 2010/0185176 A1   Jul. 22, 2010

Related U.S. Application Data

(63) Continuation of application No. 10/493,779, filed as application No. PCT/US02/34158 on Oct. 25, 2002, now Pat. No. 7,686,781.

(60) Provisional application No. 60/351,203, filed on Oct. 25, 2001.

(51) Int. Cl.
*A61M 31/00* (2006.01)

(52) U.S. Cl. ............ 604/505; 604/65; 604/508; 604/509
(58) Field of Classification Search .................. 604/503, 604/505, 508, 509, 96.01, 65
See application file for complete search history.

(56) References Cited

U.S. PATENT DOCUMENTS

| | | | | |
|---|---|---|---|---|
| 5,879,499 | A | * | 3/1999 | Corvi ............................ 156/175 |
| 6,315,768 | B1 | * | 11/2001 | Wallace ........................ 604/507 |
| 7,686,781 | B2 | * | 3/2010 | Vinten-Johansen ............ 604/65 |

* cited by examiner

*Primary Examiner* — Laura Bouchelle
(74) *Attorney, Agent, or Firm* — Emory Patent Group

(57) ABSTRACT

A catheter adapted for use in passing fluids and medicines therethrough for use in the perfusion or reperfusion of blood or blood-fluid mixtures into the arteries, veins, tissues, conduits, or organs of a patient by selectively adjusting the flow rate of fluid supplied to a drug delivery lumen of the catheter based at least in part on the sensed systemic fluid pressure and the sensed fluid pressure at a distal end of the catheter is disclosed.

39 Claims, 5 Drawing Sheets

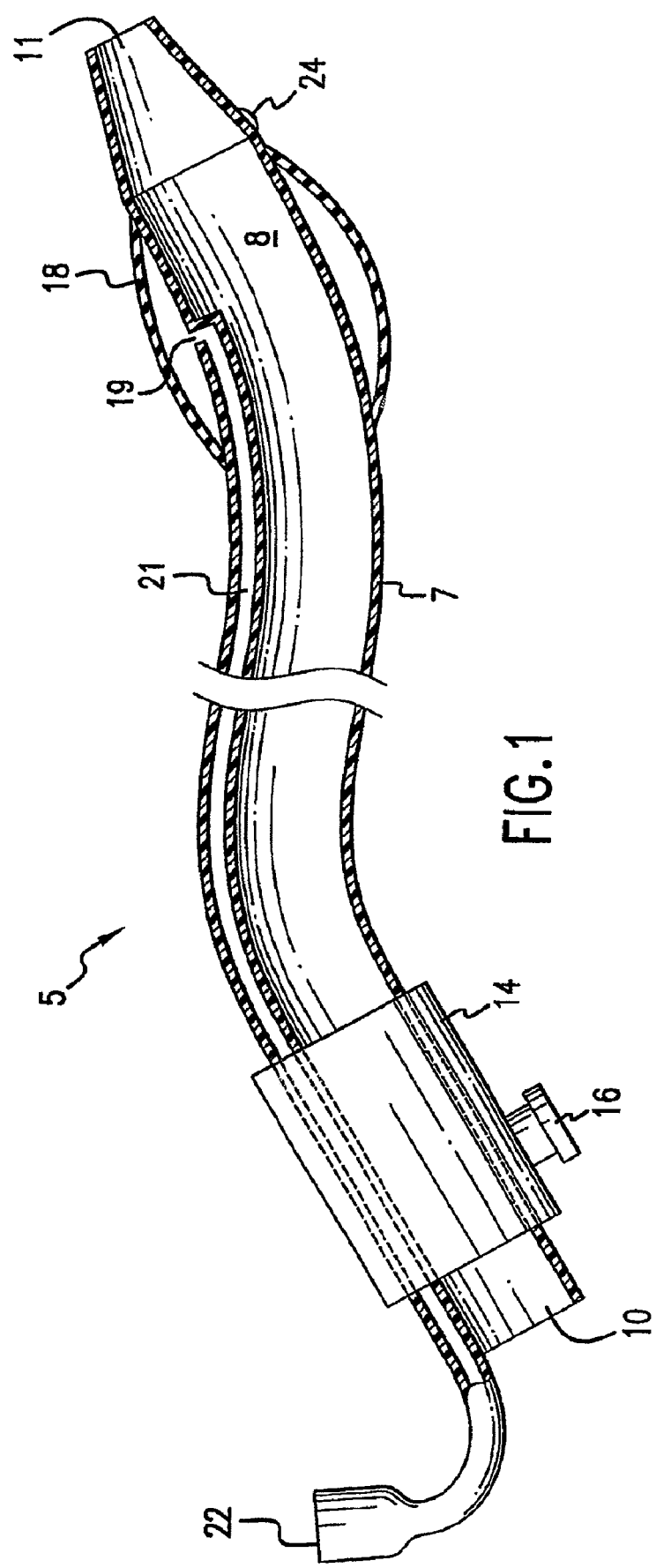

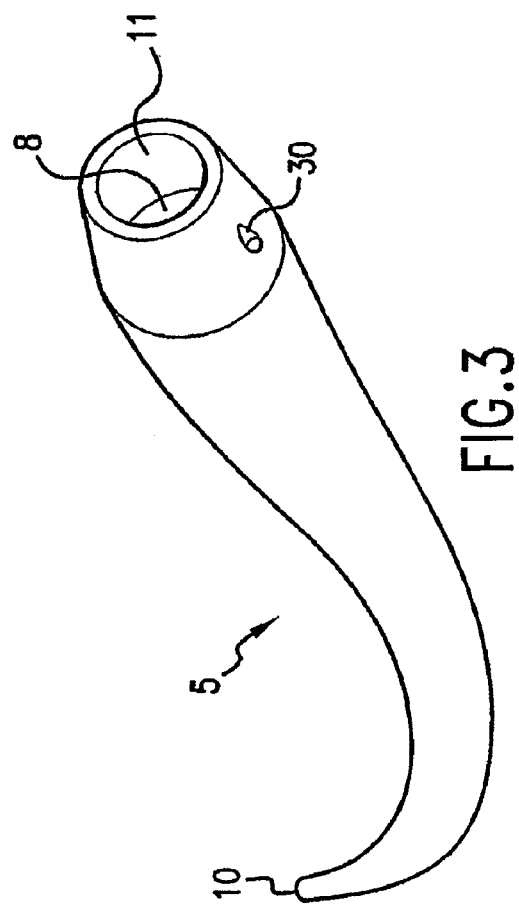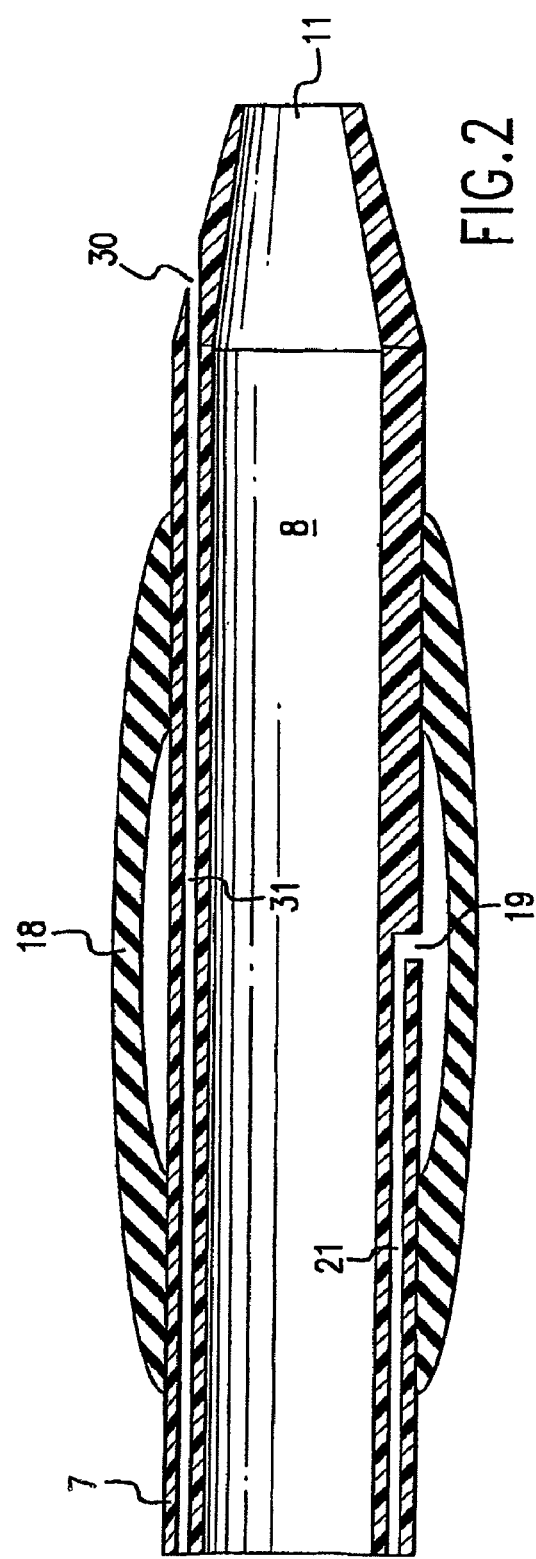

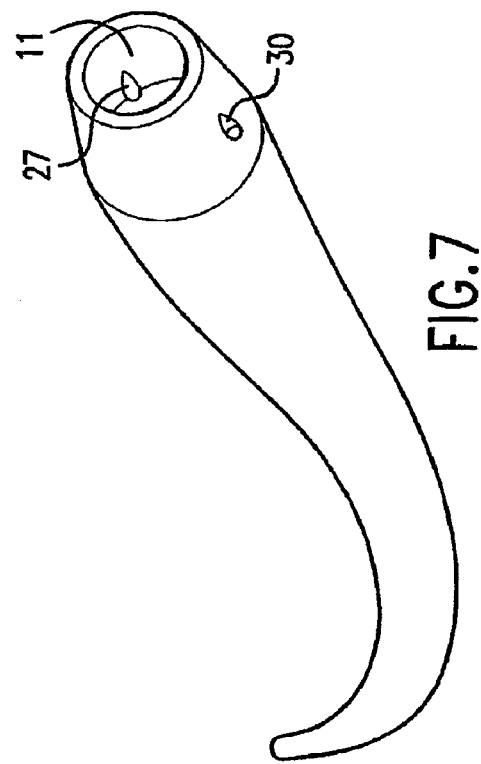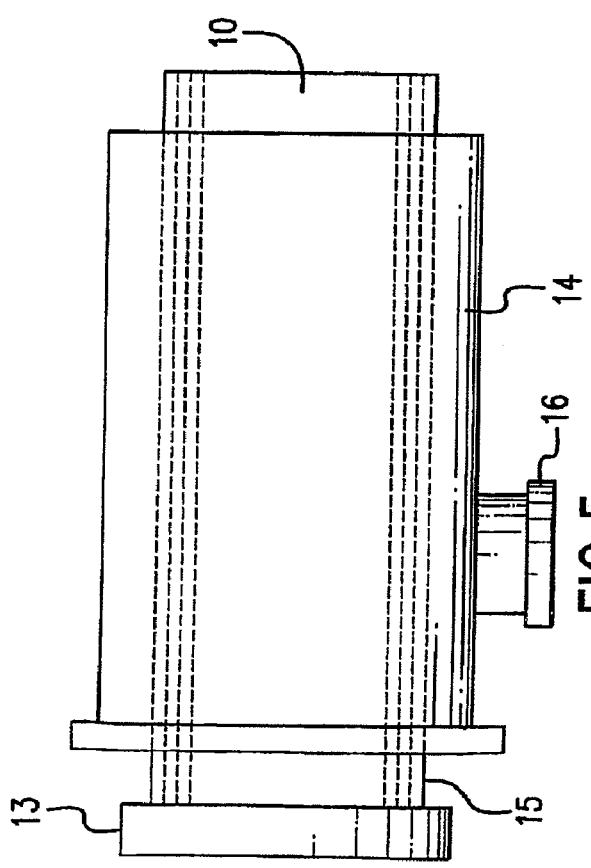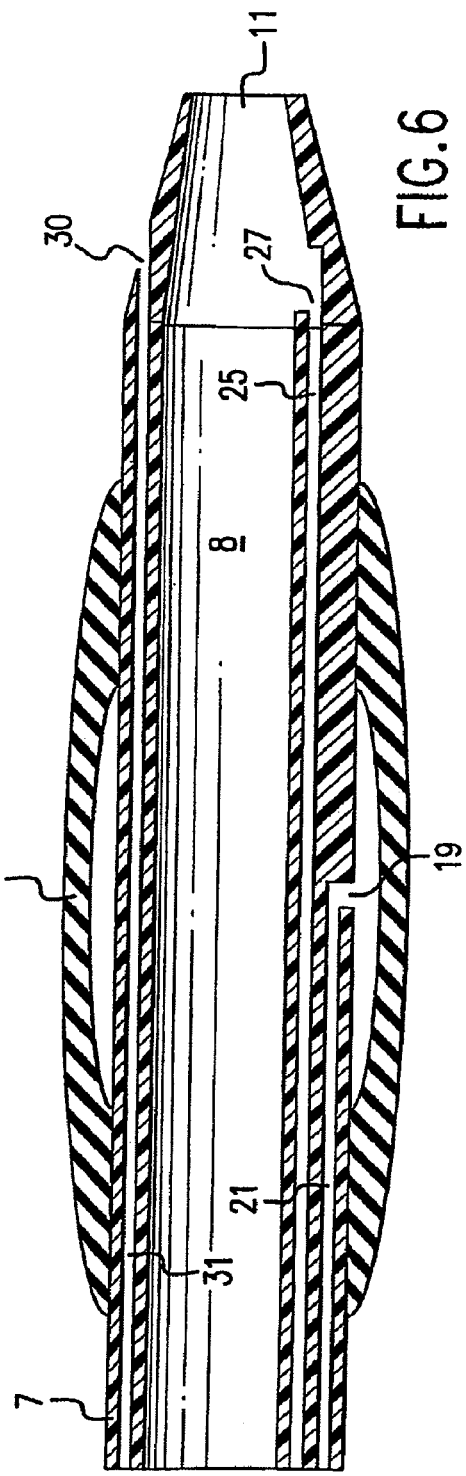

CATHETER FOR MODIFIED PERFUSION

CROSS-REFERENCE TO RELATED APPLICATION

This application is a continuation of U.S. patent application Ser. No. 10/493,779, now U.S. Pat. No. 7,686,781, which issued Mar. 30, 2010, which application claims priority to and is a National Phase Application of International Application No. PCT/US02/34158 filed Oct. 25, 2002, which claims priority to provisional U.S. Patent Application Ser. No. 60/351,203, filed on Oct. 25, 2001, in the United States Patent and Trademark Office, which applications are incorporated herein fully by this reference.

FIELD OF THE INVENTION

The present invention relates in general to medical devices. More particularly, the invention relates to a catheter adapted to pass fluids, or blood in combination with fluids, therethrough for the perfusion or reperfusion of the veins, arteries, tissues, and organs of a patient.

BACKGROUND OF THE INVENTION

The construction and use of catheters and related medical devices is well known. Current technologies allow for the catheterization of arteries and veins, and allow also for the expansion of atherosclerotic plaques in an angioplasty procedure. However, these existing technologies do not allow for the delivery of drugs, especially short-acting drugs to the target area of an organ, for example the heart. In addition, the current devices which permit the delivery of drugs do not allow for the exact control of the concentration of the drug at the site of action, because the drugs are delivered systemically and because the drug delivery may tend to vary due to the flow rate and the volume of the drug(s) being passed through the catheter. Moreover, the controlled delivery of blood, fluids or a combination thereof cannot be achieved, so the control over the conditions and compositions during perfusion or reperfusion of organs and tissues cannot be exercised.

The current embodiments of catheters, as described above, allow the application of principals of modified perfusion to organs and tissues. These principals have been developed and in use over the past 10-15 years. However, the lack of a delivery technology, or in this instance, a delivery device, has impeded the clinical application of modified perfusion and reperfusion.

What is needed, therefore, is an improved catheter constructed to permit the controlled delivery of blood, or a combination of fluids, medications and blood therethrough and into the arteries, veins, organs, or tissues of a patient, and which is also suitable for use in the modified perfusion or reperfusion of the arteries, veins, organs, or tissues of a patient.

SUMMARY

The present invention overcomes some of the design deficiencies of the known catheters by providing a catheter adapted for the controlled delivery of fluids and/or medicines therethrough and into the arteries, veins, organs, or tissues of a patient, specifically allowing delivery at known fluid pressures in the distal artery, vein or other conduit or tissue. The catheter of this invention includes an elongate tubular body defining a continuous central lumen extending through the catheter body from a proximal end to a spaced distal end thereof. A fluid-tight connector, which may for example comprise a luer-type connector, is provided at the proximal end of the tubular body and is in sealed fluid communication with the central lumen.

In use, a sheath is inserted into the access site (artery, vein or other conduit) through which the catheter is thereafter inserted. This sheath is retained in the vessel during the catheter procedure, and is provided with a port defined therein and through which the pressure in proximity to the sheath, that is the proximal pressure, may be measured. The proximal pressure measurement port may be placed into sealed fluid communication with any of the known types of fluid pressure measurement devices, as desired.

In one embodiment, an occlusive balloon is positioned to and affixed about the tubular body of the catheter, for example at the distal end thereof, and is adapted for use in known fashion. A balloon inflation port is defined within the tubular body of the catheter, and opens into the interior of the balloon. The inflation port is formed to be in sealed fluid communication with an elongate balloon inflation passageway defined within or external to the catheter body. The inflation passageway terminates at its opposite end in a balloon inlet port at the proximal end of the catheter body. The catheter may be used in conjunction with either one of a pressure wire or a flow wire, in conventional and otherwise known fashion.

In a second embodiment, a pair of spaced occlusive balloons are positioned on and about the catheter, and are adapted to be inflated or deflated together, or separately, all as desired. Separate balloon inflation ports are defined within the tubular body of the catheter, and each port opens into the interior of its respective balloon. The respective inflation ports are each formed to be in sealed fluid communication with separate and elongate balloon inflation passageways defined within, or external to, the catheter body. The inflation passageways each terminate at their opposite ends in a respective balloon inlet port at the proximal end of the catheter body.

In one embodiment, a solid state or electronic pressure sensor is affixed to the exterior of, or is otherwise embedded within, the distal end of the catheter and is adapted for measuring fluid pressure during catheterization, as well as the pressure of fluid delivery therethrough. In an alternate embodiment, a fluid filled pressure port is defined at the distal end of the catheter body and extends through a fluid filled passageway to the proximal end of the catheter body, where any known type of a fluid pressure measurement device, for example a fluid-filled transducer, adapted for use with a fluid pressure port may be used.

In yet another embodiment of the invention, the catheter is provided with an elongate drug delivery lumen defined within or external to the catheter body and separately of the central lumen. The drug delivery lumen defines a drug delivery outlet or discharge port at the distal end of the catheter in sealed fluid communication with the drug delivery lumen. The drug delivery lumen terminates at its proximal end in a drug infusion port which is also in sealed fluid communication with the drug delivery lumen. So constructed, the desired fluids may be mixed externally of and/or otherwise passed separately of the fluids within the central lumen in a controlled manner of delivery.

DESCRIPTION OF THE FIGURES

FIG. 1 is cross-sectioned view of a first embodiment of the catheter of the invention.

FIG. 2 is a cross-sectioned view of the distal end of the catheter of FIG. 1.

FIG. 3 is a perspective view of the distal end of the catheter of FIG. 1.

FIG. 5 is a partial and enlarged view of the proximal end of the catheters of FIGS. 1 and 4.

FIG. 6 is a cross-sectioned view of the distal end of the catheter of FIG. 4.

FIG. 7 is a perspective view of the distal end of the catheter of FIG. 4.

DETAILED DESCRIPTION

Figure 4:
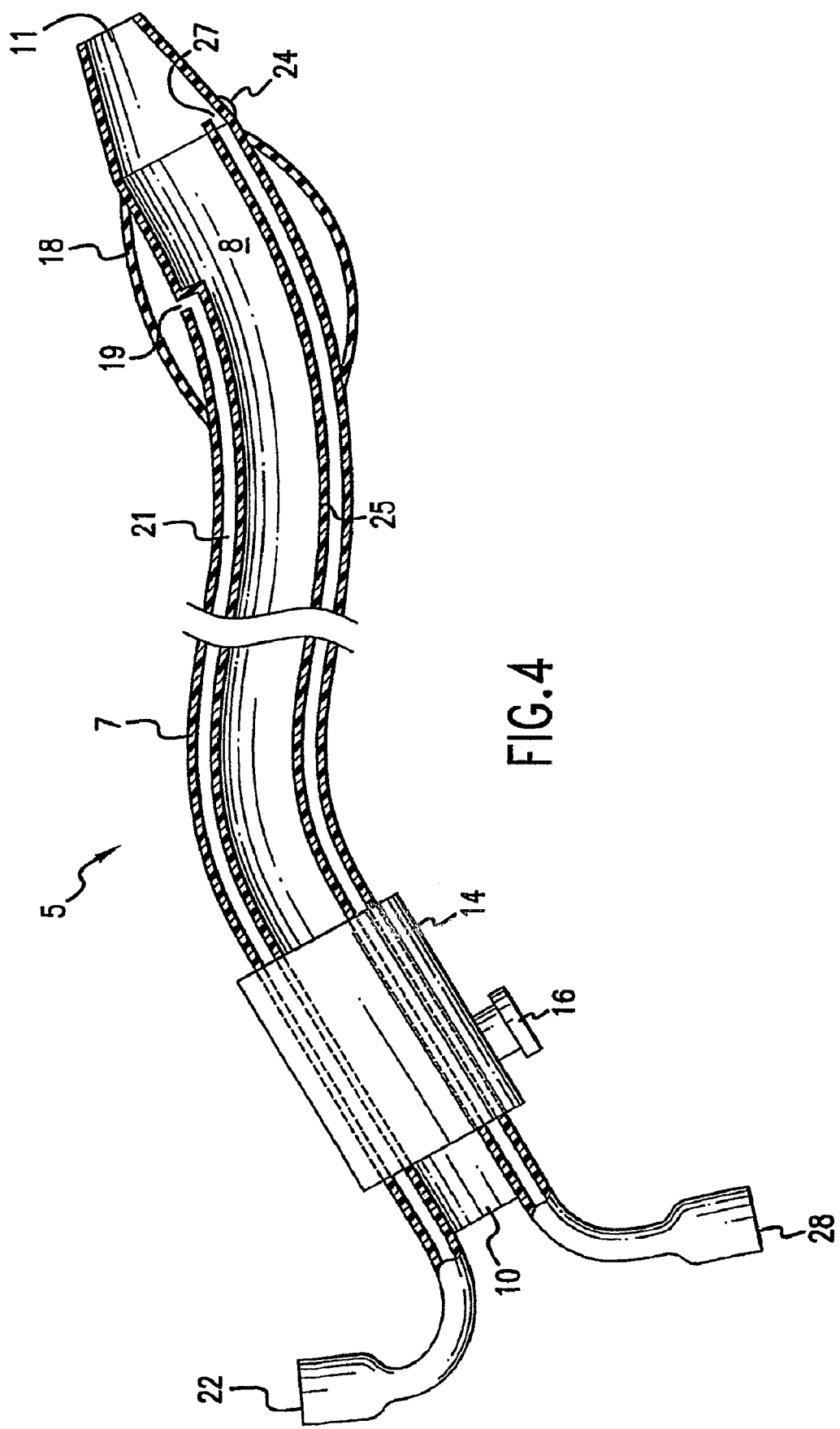
FIG. 4 is cross-sectioned view of a second embodiment of the catheter of the invention having a drug delivery lumen formed therein.

Referring now in detail to the drawings, in which like reference characters indicate like parts throughout the several views, a first embodiment of a catheter 5 of the invention is illustrated in FIGS. 1-4. The catheter is formed as an elongate tubular body 7 which defines a continuous central lumen 8 therein. The central lumen extends from a proximal end 10 of the catheter body to a spaced distal end 11 thereof The central lumen 8 is preferably designed to allow for a fluid flow therethrough, either blood or a crystalloid, or a combination thereof, of approximately 100 milliliters per minute, this flow ranging from approximately one to approximately one-hundred milliliters per minute. Also, this embodiment of the catheter, as well as the other catheter embodiments discussed herein, may be used in conjunction with either one of a pressure wire or a flow wire, in conventional and otherwise known fashion.

A luer-type of connector 13 (FIG. 5) is provided at the proximal end of the catheter, and which is constructed in known fashion for receiving in sealed fluid-tight communication the supply line(s) for the fluid(s) to be passed through the central lumen. The proximal end of the catheter is also provided with a proximal insertion sheath 14 extended about the exterior surface of the catheter, with a septum 15 (FIG. 5) sealing the sheath about the catheter.

The proximal insertion sheath allows the catheter to be inserted into the vessel for ultimate vascular access of the target vessel or organ. It is modified to allow measurement of vascular pressure in the vicinity of the insertion of the sheath. The sheath is similar to those currently used to insert catheters by the Seldinger technique, in which a guide wire is inserted into the access vessel from a percutaneous approach or direct cut-down, and over which a guide catheter and a stylet are inserted into an artery or vein convenient for use as an access. The stylet (not shown) is subsequently removed as the guidewire and guide catheter are advanced.

The septum 15 at the proximal end of the sheath closes to prevent the flow of blood from inside the vessel to the outside. The guidewire, followed by the perfusion catheter, is then inserted through the septum which seals around the wire and catheter to maintain hemostasis. The guidewire and catheter are then advanced toward the target vessel in known fashion, for example, as used in angioplasty or angiographic procedures. The perfusion catheter may be used in conjunction with a guide catheter for procedures performed in known fashion for angioplasty and/or other coronary catheterization procedures. In addition, the perfusion catheter may be used in conjunction with, or in lieu of an angioplasty catheter to cross the plaque site and expand the site of stenosis using the catheter balloons.

The sheath 14 includes an outlet or a pressure measurement port 16 defined therein for use in measuring the vessel blood pressure near the proximal end of the catheter in association with any of the known types of fluid pressure measurement devices (not illustrated) adapted to be received thereat. The port 16 may be fashioned as a luer-type of connector, if so desired. The pressure sheath 14 in association with the outlet port 16 may thus be used to measure and/or monitor the proximal arterial or venous blood pressure of the patient, or used as a target pressure for use in adjusting the fluid pump rates to in turn control the distal, arterial or venous fluid flow rate and pressures. In addition, the port 16 may be used as a general intravenous access for administration of fluids or drugs.

An occlusive balloon 18 of known construction is carried on and extends about the tubular body of the catheter intermediate the proximal and the distal ends, respectively, of the catheter as illustrated in FIGS. 1, 2, 4, and 6. A balloon inflation port 19 is defined within the body of the catheter in sealed fluid/air-tight communication with the balloon interior. An elongate balloon inflation passageway 21 is defined within or otherwise formed as a part of the catheter body separate of the central lumen. The passageway 21 is a hydraulic passageway in fluid communication with the balloon inflation port, and extends to a balloon inlet port 22 situated at the proximal end of the catheter (FIG. 1), to which a known type of balloon inflation device (not illustrated) may be attached.

As shown in FIGS. 1 and 4, a solid state pressure sensor 24 may be affixed to the exterior of, or otherwise formed, positioned, or embedded within the distal end of the catheter body, and is adapted for use in measuring the target or ambient fluid pressure(s) at the distal or treatment end of the catheter during catheterization, as well as during the infusion of any fluids through the distal end of the catheter and into the arteries, veins, organs, or tissues of the patient. The distal pressure sensor may thus comprise any one of the known types of solid-state transducers for sensing and transmitting high fidelity pressure signals such as those manufactured by Millar Instruments, Inc. of Houston, Tex., as well as any other type of solid state transducer which is adapted for use in pressure or tactile sensation measurement. The lead wires of the sensor 24 are passed to a suitable plug (not illustrated) positioned at the proximal end of the catheter, and may therefore be passed through a communications channel 49 (FIG. 8) defined within the body of the catheter, or through an existing passageway, for example the passageway 31 (FIGS. 2 and 6) of the fluid-filled pressure sensor available for use with the catheter of this invention.

Referring now to FIGS. 2 and 6, an alternate embodiment of the catheter is disclosed having an alternate means for measuring the pressure at the distal end of the catheter. As shown in these two figures, the distal end of the catheter is provided with a fluid-filled distal pressure port 30 defined therein and extending in sealed fluid (hydraulic) communication through a passageway 31, defined within the catheter, to a suitable discharge port (not illustrated), for example a luer type of port, to which a suitable fluid pressure measurement device, for example one of the known types of fluid-filled transducers, is connected. The use of fluid filled passageways, and of fluid-filled pressure ports for measuring fluid pressures is well known and within the scope of those skilled in the art, and thus is not described in greater detail herein.

Referring now to FIGS. 4 and 6, yet another embodiment of the catheter of this invention is disclosed. In this embodiment of the catheter a distal drug outlet or delivery port 27 is defined within an elongate drug delivery lumen 25 defined within and extending in the lengthwise direction of the catheter body. The drug delivery lumen 25 is defined within the catheter body separately of the central lumen 8 thereof such that the fluids passed therethrough will not mix with those within the central lumen, but will instead be mixed at the distal tip of the catheter. The drug delivery port is formed to be in sealed fluid-tight communication with the drug delivery lumen. The drug delivery lumen also has a drug infusion port 28 defined therein, as illustrated in FIG. 4, for the passage of drugs or drug-fluid admixtures therethrough and into the drug delivery lumen.

So provided, the drug delivery lumen allows for the delivery of fast-acting, and/or rapidly degrading drugs through the distal end of the catheter, and into the treatment area within the surrounding arteries, veins, organs, or tissues of the patient. Examples of fast-acting and/or rapidly degrading drugs of the type that may be used with the invention include, but are not limited to, adenosine and nitric oxide. The distal infusion of these drugs through the drug lumen will prevent these short-acting agents from being metabolized or otherwise degraded by blood or other fluids during transit in the catheter lumen, and/or will prevent the interaction of the drugs before they enter the patient's blood stream, organs, or tissues.

In use, the catheter is introduced into the appropriate arterial or venous vasculature and guided to the target area through a pre-placed sheath-and-guidewire, and guided to the target location in known fashion. In a first method of use therefore, the catheter may be fluoroscopically guided into a coronary artery that is partially or entirely blocked. The catheter is positioned at the point of occlusion, and the occlusive balloon is inflated as it is used in an angioplasty procedure, for example. In one embodiment of the procedure, the balloon can then be deflated and a cardioprotective agent may be infused at the physician's discretion to attenuate reperfusion injury or arrhythmias, or to introduce a local anti-arrhythmic or local inotropic agent.

In an alternate method of use, the catheter can be placed across the blockage and then inflated as per the use of an angioplasty catheter, and left deployed to introduce blood, fluids, or blood-fluid mixtures therethrough while preventing the admixture of native blood and blood flow therewith. The blood or blood-fluid mixture may contain cardioprotective drugs or anti-arrhythmic drugs to once again attenuate reperfusion injury, and so on. If so desired, blood or blood-fluid mixtures (i.e., hemodiluted blood) can be introduced through the catheter to prevent ischemia during the period of occlusive balloon inflation. As known, the benefit of including blood in a blood-fluid mixture is that oxygen is provided to the tissue, nutrients and endogenous substrates are included, as are endogenous anti-oxidants. Also, the flow rate and the pressure of the fluid can be controlled to stay within physiological and target therapeutic limits.

The complete occlusion of the blood vessel allows the physician to control the composition of the perfusion fluid, its flow rate, and pressure to the distal tissue or organ. In another embodiment of the procedure, the balloon may be partially deflated, or deflated according to a specified time algorithrim proceeding from full inflation to full deflation to allow for controlled blood flows. In addition, the time duration of inflation can be controlled by appropriate and known types of balloon inflation-deflation devices connected to the proximal end of the catheter at the luer lock (or other configuration) port.

By providing the drug delivery lumen 25, in association with the drug delivery port 27, rapidly deactivated drugs may be passed therethrough which allows for the admixture of drugs at the tip, i.e., the distal end, of the catheter rather than in the proximal portion thereof, or in the delivery device (not illustrated) affixed to the fluid-tight connector at the proximal end of the catheter. The desired drug or drugs will be infused through the drug infusion port 28 at the proximal end of the catheter, and outside of the patient's body.

Figure 8:
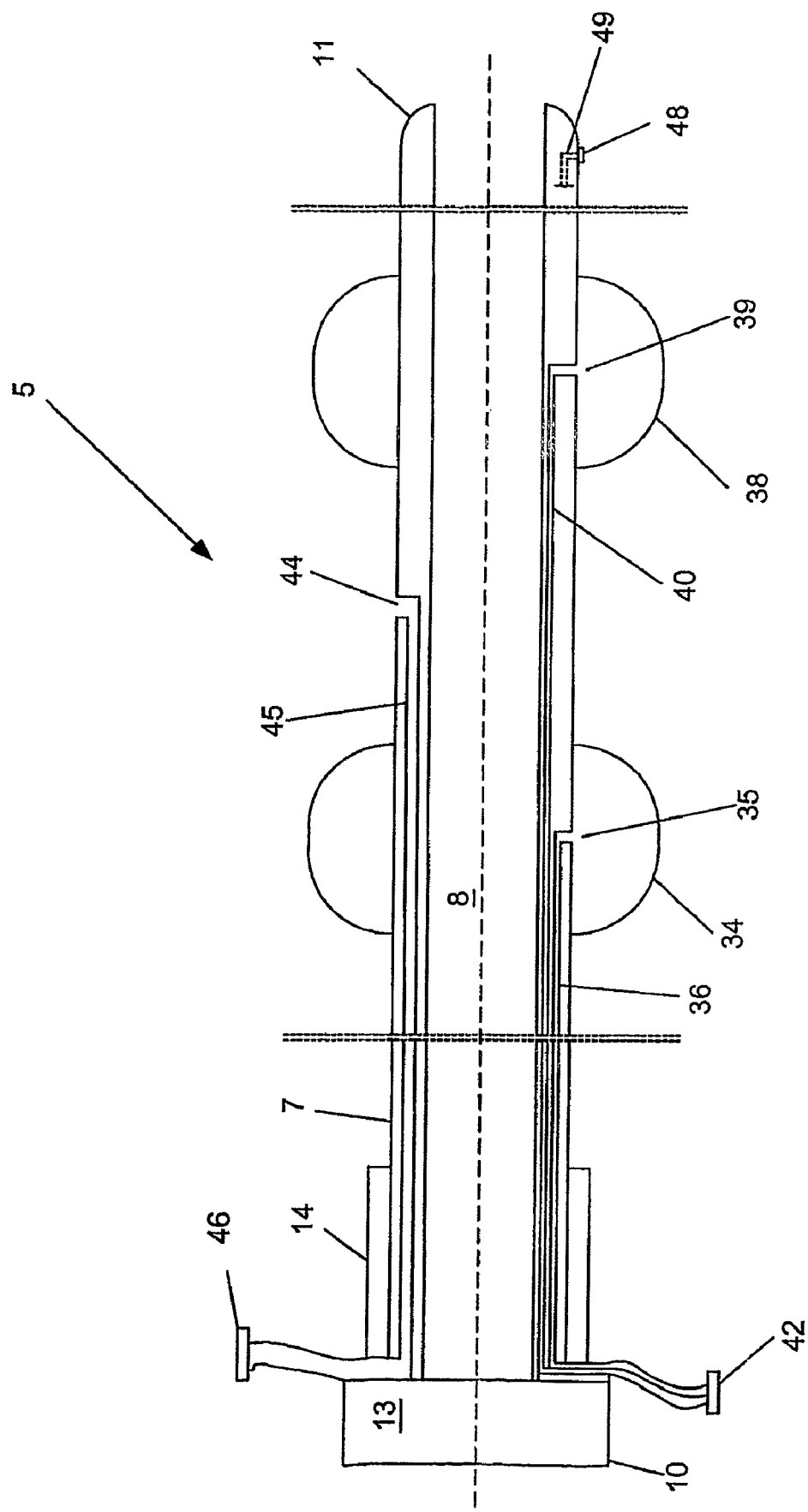
FIG. 8 is a cross sectional view of a two occlusive balloon embodiment of the catheter of the invention.

Referring now to FIG. 8, a double balloon, or two balloon, embodiment of the catheter is illustrated. In this configuration a second occlusive balloon is spaced from the first occlusive balloon by a distance in the range of from approximately 0.5 to approximately 10 centimeters. This construction allows for the accumulation of fluids within this "inter-balloon" space. So constructed, this embodiment of the catheter allows for the measured delivery of medications into a target vessel wall by exposing the wall directly to the medications such that the inter-balloon space is used for accumulating the fluids and/or medications passed therein and that will, for example, bathe the vascular wall, the endothelium, or the plaque-containing area of the vessel wall.

The fluids/medications passed into the balloon inter-space can be retained in this space for a specified time, therefore allowing higher concentrations of the desired medications to be used than would otherwise be tolerated if given systemically. Thereafter, the medications/fluids can be re-aspirated into the catheter so that they are not delivered to the body, or can simply be washed into the general circulation when the balloons are deflated. The procedure for elimination of the medications used in the space between the balloons depends on toxicity and side effects of the medications. Applications using this construction of the balloon catheter include, but are not limited to, treatment for restenosis, localized endothelial injury, the stabilization of a plaque/plaque rupture, local coagulation, stabilization of the vascular endothelium by preventing inflammatory activation, attenuating cell proliferation by contact with anti-proliferative agents, delivery of gene therapy directly to the vessel wall, or other localized changes in the vessel wall or its constituents. In another application of this double balloon device, the space between the two balloons (the balloon inter-space) can be placed at the branch-point of a vessel, so that the fluid or drugs infused into this space, confined by the two balloons, will be selectively distributed into that branch.

Referring to FIG. 8, therefore, the catheter 5 is once again shown as having the elongate tubular body 7 with the continuous central lumen 8 defined therein extending from the proximal end 10 of the catheter body to the distal end 11 thereof. The catheter of FIG. 8 has a first occlusive balloon 34 positioned on the catheter body. intermediate the proximal and distal ends thereof An inflation port 35 is defined within the catheter body in fluid communication with a passageway 36 defined within the catheter body, and which extends to the proximal end thereof A second occlusive balloon 38 is also positioned on the catheter body, intermediate the first balloon 34 and the distal end of the catheter. A second balloon inflation port 39 is defined within the tubular body of the catheter in fluid communication with a passageway 40 defined within the catheter body and extending to the proximal end thereof.

Each of the passageways 36, 40 are formed separately of one another, and each is also constructed to be placed into sealed fluid communication with a balloon inlet port or lumen 42 constructed to inflate the balloons 34,38, respectively, separately or together, as desired. An inflation syringe or bulb (not illustrated) will be attached to the inflation lumen 42 for inflating the occlusive balloons, and is constructed to allow for the inflation and/or deflation of the balloons separately or together, as desired, the syringe being of known construction and used in known fashion.

A drug delivery port 44 is defined within the catheter body such that it is positioned between the occlusive balloons 34 and 38, in what has been referred to as the balloon inter-space.

The drug delivery port is in sealed fluid communication with a passageway 45 defined within the catheter body, which passageway extends in sealed fluid communication to a drug infusion port 46 at the proximal end of the catheter. The desired fluids, for example blood or blood-fluid mixtures, or drug admixtures, are therefore mixed externally of the catheter and are then passed into the drug infusion port, through the passageway 45, and exit the catheter body from the drug delivery port once at least one, or both, of the occlusive balloons have been inflated, as described in greater detail below.

Still referring to FIG. 8, the catheter is shown with a distal pressure sensor 48, which pressure sensor may be a solid-state sensor or a fluid-filled pressure port of the types described in greater detail above. The fluid-filled or solid-state pressure sensors are optional embodiments of the catheter. A conduit/passageway 49 is defined within the catheter body and extends from the pressure sensor to the proximal end of the catheter for connection to a suitable pressure measurement device of known construction for the type of pressure sensor being used. If, for example, a solid-state pressure sensor is used, the lead wires (not illustrated) which would extend from the sensor will be passed through the conduit 49 to the proximal end of the catheter body. Alternately, and if so desired, the lead wires from the solid-state pressure sensor may instead be embedded within the wall of the catheter body rather than passed through the conduit/passageway 49. If the pressure sensor is a fluid-filled port, however, then the passageway 49 will also be fluid-filled and will extend to a suitable fluid pressure measurement device (not illustrated), as known.

The method of using the two-balloon catheter of FIG. 8 includes the steps of inserting the catheter into the desired artery, vein, vessel or conduit within the body for treating a segment of the conduit by isolating the target segment through the inflation of the two occlusive balloons. Once the balloons are inflated, the desired blood, fluids, and/or medications are injected into the catheter and passed through the drug delivery port into the inter-space between the balloons to "dwell" in this area. As the volume of this area is known, a corresponding and pre-determined volume of the desired fluids/drugs can be injected into the inter-balloon area to prevent the spillover and possible distribution of the fluids/drugs into the patient or system beyond this defined area. Thereafter, the medications may be evacuated from the inter-space back through the drug delivery port in order to avoid any toxicity, or the medications may be allowed to wash out into the system by deflating the balloons if appropriate. This construction is useful where the catheter diameter may not support the flow of blood therethrough, i.e., the catheter is a low-profile configuration, and may also allow for the delivery of blood, fluids, and/or combinations therethrough to metabolically support the distal tissue and prevent ischemia therein, or provide for the delivery of tissue-protective medications.

It is anticipated that either or both of the pressure sensor arrangements described herein may be used with any one of the several embodiments of the catheter of the invention described herein, as desired. It is also anticipated that the catheter of the invention may be used with or without a drug delivery lumen formed as a part thereof, if so desired. Accordingly, it is anticipated that the catheter of this invention may be used with any desired one or combination of a distal pressure sensor and/or a drug delivery lumen as disclosed hereinabove, as well as with one or two occlusive balloons, as described in greater detail below. Therefore, the catheter of the invention may include any one or combination of the several features disclosed hereinabove in a single catheter, as desired.

The catheter 5, in all of its embodiments as illustrated in FIGS. 1-8 hereof, is constructed of known materials, which materials are particularly suited for, and approved for use in surgical or intravascular procedures. The central lumen 8 of the catheter is sized sufficiently for the delivery of fluids, blood, or blood-fluid mixtures therethrough. The occlusive balloons 18, 34, and 38, respectively, are each sized and shaped so that they may be inflated through their respective balloon inflation ports 19, 35, and 39 such that the respective balloons seal the artery or vein within which they are received, and to also allow for the infusion of the desired blood, or blood-fluid mixtures in a controlled manner through the catheter and into the veins, arteries, conduits, or tissues without the admixture of blood in the proximal portion of the catheter. The respective balloons can also be partially inflated to allow for a mixture of the blood from the patient's vessel with any crystalloid or drugs passed through the central lumen and/or the drug delivery lumen.

Each of the distal pressure sensors 24 and 49, as well as the distal pressure port 30, can be used to measure the distal fluid pressures in the vessel or organ during catheterization or infusion of the blood, fluid, or blood-fluid mixtures into the patient, and can also be used to control the flow rate of fluid therethrough if, for example, a separate infusion pump or device (not illustrated) is being used. In the alternative, the distal pressure sensor may be used to measure the distal fluid pressures for the determination and the calculation of the coronary or other vascular reserves thereat, or other vascular indices in which pressure is used as a coefficient.

Although several embodiments of the invention have been disclosed in the foregoing specification, it is understood by those skilled in the art that many modifications and other embodiments in the invention will come to mind to which the invention pertains, having the benefit of the teaching presented in the foregoing description and the associated drawings. It is thus understood that the invention is not limited to the specific embodiments disclosed hereinabove, and that many modifications and other embodiments are intended to be included within the scope of the invention. Moreover, although specific terms are employed herein, they are used only in a generic and descriptive sense, and not for the purposes of limiting the described invention, and the words "a," "and," or "the" as they appear hereinabove may mean one or more, depending upon the context in which the words are used.

I claim:

1. A method of using a catheter to pass fluids therethrough and into an artery, vein, organ or the tissues of a patient, said method comprising:
   introducing a catheter into the desired artery, vein, conduit, organ or tissue of the patient, the catheter comprising an elongate tubular body defining a central lumen extending from a proximal end to a distal end of the body;
   sensing fluid pressure thereat the distal end of the body;
   sensing a systemic fluid pressure in the patient proximate to the proximal end of the body; and
   selectively adjusting the flow rate of fluid supplied to the central lumen of the catheter based at least in part on the sensed systemic fluid pressure and the sensed fluid pressure at the distal end of the body.

2. The method of claim 1, further comprising:
   selectively inflating a first occlusive balloon disposed on an exterior of the elongate tubular body.

3. The method of claim 1, wherein the catheter further comprises a drug delivery lumen defined within said body separately of said central lumen and extending in the lengthwise direction of said body, a drug delivery outlet proximate the distal end of the body in fluid communication with the drug delivery lumen, and a drug infusion port in fluid communication with the drug delivery lumen, and further comprising selectively adjusting the flow rate of fluid supplied to the drug delivery lumen of the catheter based at least in part on the sensed systemic fluid pressure and the sensed fluid pressure at the distal end of the body.

4. The method of claim 1, wherein the step of sensing the systemic fluid pressure in the patient proximate to the proximal end of the body comprises positioning a sheath, which extends about an exterior periphery of the body approximate the proximal end of the body, in fluid communication with the vascular system of the patient.

5. The method of claim 4, wherein the sheath defines a sheath outlet port therein, and wherein the step of sensing a systemic fluid pressure in the patient proximate to the proximal end of the body further comprises placing a pressure measurement device in sealed fluid communication with the sheath outlet port.

6. The method of claim 1, wherein the step of sensing fluid pressure thereat the distal end of the body comprises a pressure measurement device configured to sense fluid pressure thereat the distal end of the body.

7. The method of claim 6, said the pressure measurement device comprises a solid-state pressure measurement device.

8. The method of claim 7, wherein the solid-state pressure measurement device is embedded within the tubular body of the catheter.

9. The method of claim 7, wherein the solid-state pressure measurement device comprises a transducer.

10. The method of claim 6, said the pressure measurement device comprises a fluid-filled pressure port.

11. The method of claim 1 or 3, wherein the flow rate of fluid delivered by the catheter is selectively adjusted to maintain the sensed fluid pressure at the distal end of the body substantially equal to the sensed systemic pressure.

12. The method of claim 3, further comprising controlling the flow rates of fluid supplied to the respective central lumen and drug delivery lumen to control the relative composition of the fluid exiting the catheter, and wherein the flow rate of fluid delivered by the catheter is selectively adjusted to maintain the sensed fluid pressure at the distal end of the body substantially equal to the sensed systemic pressure.

13. A method of passing fluids into an occluded artery or vein, said method comprising:
 introducing a catheter having a proximal end and a spaced distal end into the desired arterial or venous vasculature;
 positioning the distal end of the catheter proximate the point of the occlusion;
 inflating an occlusive balloon disposed on the exterior of the catheter;
 sensing fluid pressure thereat the distal end of the catheter;
 sensing a systemic fluid pressure in the patient proximate to the proximal end of the catheter; and
 selectively adjusting the flow rate of fluid supplied to a central lumen defined within the catheter and extending from the proximal end to the distal end of the catheter based at least in part on the sensed systemic fluid pressure and the sensed fluid pressure at the distal end of the catheter.

14. The method of claim 13, further comprising deflating the occlusive balloon prior to passing the fluid through the central lumen.

15. The method of claim 13, further comprising:
 passing at least one fluid through a drug delivery lumen defined within the catheter separately of the central lumen;
 delivering the at least one fluids into the arterial or venous vasculature through a drug delivery outlet defined proximate the distal end of the catheter and in fluid communication with the drug delivery lumen; and
 selectively adjusting the flow rate of fluid supplied to the drug delivery lumen based at least in part on the sensed systemic fluid pressure and the sensed fluid pressure at the distal end of the catheter.

16. The method of claim 15, further comprising passing the at least one fluid into a drug infusion port in fluid communication with the drug delivery lumen.

17. The method of claim 13 or 15, wherein the flow rate of fluid delivered by the catheter is selectively adjusted to maintain the sensed fluid pressure at the distal end of the body substantially equal to the sensed systemic pressure.

18. The method of claim 15, further comprising controlling the flow rates of fluid supplied to the respective central lumen and drug delivery lumen to control the relative composition of the fluid exiting the catheter, and wherein the flow rate of fluid delivered by the catheter is selectively adjusted to maintain the sensed fluid pressure at the distal end of the body substantially equal to the sensed systemic pressure.

19. The method of claim 18, further comprising:
 mixing the at least one fluid together externally of the catheter; and
 passing the mixed at least one fluid into the drug infusion port.

20. A method of passing fluids into an occluded or narrowed artery or vein, said method comprising:
 introducing a catheter having a proximal end and a spaced distal end into the desired arterial or venous vasculature;
 positioning the distal end of the catheter across the point of the occlusion or narrowing;
 inflating an occlusive balloon disposed on the exterior of the catheter;
 sensing fluid pressure thereat the distal end of the catheter;
 sensing a systemic fluid pressure in the patient proximate to the proximal end of the catheter; and
 selectively adjusting the flow rate of fluid supplied to a central lumen defined within the catheter and extending from the proximal end to the distal end of the catheter based at least in part on the sensed systemic fluid pressure and the sensed fluid pressure at the distal end of the catheter.

21. The method of claim 20, further comprising:
 passing at least one fluid through a drug delivery lumen defined within the catheter separately of the central lumen;
 delivering the at least one fluids into the arterial or venous vasculature through a drug delivery outlet defined proximate the distal end of the catheter and in fluid communication with the drug delivery lumen; and
 selectively adjusting the flow rate of fluid supplied to the drug delivery lumen based at least in part on the sensed systemic fluid pressure and the sensed fluid pressure at the distal end of the catheter.

22. The method of claim 21, further comprising passing the at least one fluid into a drug infusion port in fluid communication with the drug delivery lumen.

23. The method of claim 20 or 21, wherein the flow rate of fluid delivered by the catheter is selectively adjusted to maintain the sensed fluid pressure at the distal end of the body substantially equal to the sensed systemic pressure.

24. The method of claim 21, further comprising controlling the flow rates of fluid supplied to the respective central lumen and drug delivery lumen to control the composition of the fluid exiting the catheter, and wherein the flow rate of fluid delivered by the catheter is selectively adjusted to maintain the sensed fluid pressure at the distal end of the body substantially equal to the sensed systemic pressure.

25. The method of claim 20, wherein the catheter is positioned after resolving the occlusion or narrowing.

26. The method of claim 20, wherein the catheter is positioned before resolving the occlusion or narrowing.

27. A method of passing fluids into the vascular system of a subject, said method comprising:
  introducing a catheter having a proximal end and a spaced distal end into a desired vessel of the vascular system;
  positioning the distal end of the catheter at a desired position within the vascular system;
  inflating an occlusive balloon disposed on the exterior of the catheter so selectively fixate the distal end of the catheter at the desired position;
  sensing fluid pressure thereat the distal end of the catheter;
  sensing a systemic fluid pressure in the patient proximate to the proximal end of the catheter; and
  selectively adjusting the flow rate of fluid supplied to a central lumen defined within the catheter and extending from the proximal end to the distal end of the catheter based at least in part on the sensed systemic fluid pressure and the sensed fluid pressure at the distal end of the catheter.

28. The method of claim 27, further comprising:
  passing at least one fluid through a drug delivery lumen defined within the catheter separately of the central lumen;
  delivering the at least one fluids into the vascular system through a drug delivery outlet defined proximate the distal end of the catheter and in fluid communication with the drug delivery lumen; and
  selectively adjusting the flow rate of fluid supplied to the drug delivery lumen based at least in part on the sensed systemic fluid pressure and the sensed fluid pressure at the distal end of the catheter.

29. The method of claim 28, further comprising passing the at least one fluid into a drug infusion port in fluid communication with the drug delivery lumen.

30. The method of claim 27 or 28, wherein the flow rate of fluid delivered by the catheter is selectively adjusted to maintain the sensed fluid pressure at the distal end of the body substantially equal to the sensed systemic pressure.

31. The method of claim 27, further comprising controlling the flow rates of fluid supplied to the respective central lumen and drug delivery lumen to control the relative composition of the fluid exiting the catheter.

32. The method of claim 31, wherein the flow rate of fluid delivered by the catheter is selectively adjusted to maintain the sensed fluid pressure at the distal end of the body substantially equal to the sensed systemic pressure.

33. The method of claim 27, wherein the catheter is positioned relative to an occluded or narrowed artery or vein of the vascular system.

34. The method of claim 33, wherein the catheter is positioned after resolving the occlusion or narrowing.

35. The method of claim 33, wherein the catheter is positioned before resolving the occlusion or narrowing.

36. A method of passing fluids into the vascular system of a subject, said method comprising:
  introducing a catheter having a proximal end and a spaced distal end into a desired vessel of the vascular system;
  positioning the distal end of the catheter at a desired treatment position within the vascular system;
  inflating a first occlusive balloon disposed on the exterior of the catheter so selectively fixate the distal end of the catheter at the desired treatment position;
  inflating a second occlusive balloon disposed on the exterior of the body and spaced from said first balloon;
  passing fluids through the catheter and into a space defined within the vascular system by and between the first occlusive balloon and the second occlusive balloon respectively;
  sensing fluid pressure thereat the distal end of the catheter;
  sensing a systemic fluid pressure in the patient proximate to the proximal end of the catheter; and
  selectively adjusting the flow rate of fluid supplied to a central lumen defined within the catheter and extending from the proximal end to the distal end of the catheter based at least in part on the sensed systemic fluid pressure and the sensed fluid pressure at the distal end of the catheter.

37. The method of claim 36, further comprising treating a target segment of the vascular system by isolating the target segment with the two occlusive balloons.

38. The method of claim 36, further comprising injecting the fluids into the defined space between the two occlusive balloons.

39. The method of claim 36, further comprising permitting the fluids to dwell in the defined space between the two occlusive balloons.

* * * * *